(12) United States Patent
Newton

(10) Patent No.: US 10,937,543 B1
(45) Date of Patent: Mar. 2, 2021

(54) SYSTEMS AND METHODS FOR PREDICTIVE AND AUTOMATED AND CENTRALIZED REAL-TIME EVENT DETECTION AND COMMUNICATION

(71) Applicant: TeleTracking Technologies, Inc., Pittsburgh, PA (US)

(72) Inventor: Scott Newton, Pittsburgh, PA (US)

(73) Assignee: TeleTracking Technologies, Inc., Pittsburgh, PA (US)

( * ) Notice: Subject to any disclaimer, the term of this patent is extended or adjusted under 35 U.S.C. 154(b) by 161 days.

(21) Appl. No.: 15/958,584

(22) Filed: Apr. 20, 2018

Related U.S. Application Data

(60) Provisional application No. 62/488,015, filed on Apr. 20, 2017.

(51) Int. Cl.
*G16H 40/20* (2018.01)
*G06Q 10/04* (2012.01)
*G16H 80/00* (2018.01)
*G06Q 10/06* (2012.01)
*G06Q 10/08* (2012.01)

(52) U.S. Cl.
CPC ............. *G16H 40/20* (2018.01); *G06Q 10/04* (2013.01); *G06Q 10/06311* (2013.01); *G06Q 10/06375* (2013.01); *G06Q 10/083* (2013.01); *G16H 80/00* (2018.01)

(58) Field of Classification Search
CPC .. G16H 40/20; G16H 80/00; G06Q 10/06311; G06Q 10/083; G06Q 10/04; G06Q 10/06375
See application file for complete search history.

(56) References Cited

U.S. PATENT DOCUMENTS

2008/0312972 A2* 12/2008 Rosow ................... G16H 40/20
705/5
2010/0198609 A1* 8/2010 Mellin ................... G06Q 10/06
705/2

* cited by examiner

*Primary Examiner* — Linh Giang Le
(74) *Attorney, Agent, or Firm* — Ference & Associates LLC

(57) ABSTRACT

Systems and methods for implementing a healthcare command center in a healthcare venue such as a hospital are disclosed. A healthcare command center may provide a number of services to the healthcare venue or to a healthcare system, such as a system including multiple healthcare venues. Services may be selected according to the needs and capacity of a healthcare venue or system. A healthcare command center may provide all available services and tools to a healthcare venue or system. Services and tools may span a continuum of care from community health to preventative health to acute care to post-acute care to reintegration of patients back into the community.

20 Claims, 1 Drawing Sheet

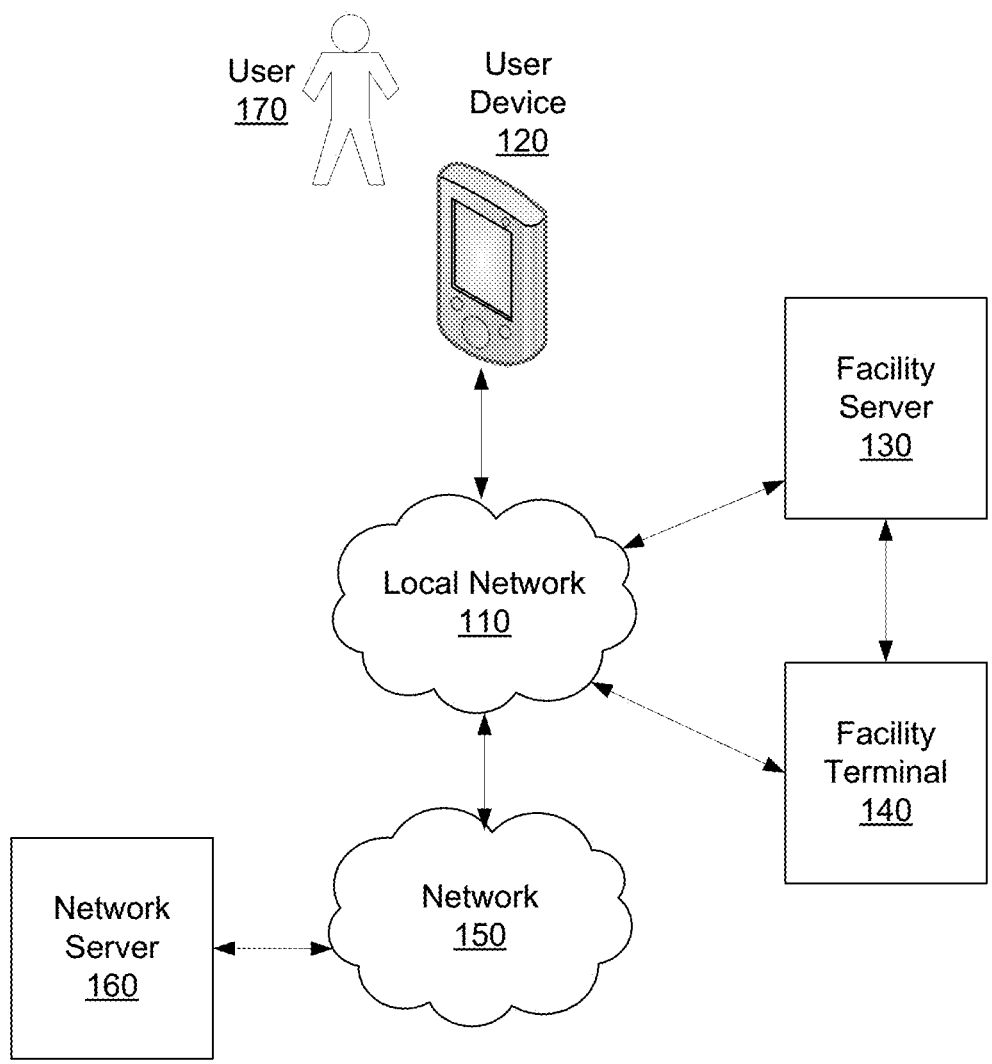

SYSTEMS AND METHODS FOR PREDICTIVE AND AUTOMATED AND CENTRALIZED REAL-TIME EVENT DETECTION AND COMMUNICATION

CROSS-REFERENCES TO RELATED APPLICATIONS

This application claims priority from U.S. Provisional Patent Application No. 62/488,015, filed Apr. 20, 2017, which is hereby incorporated by reference in its entirety.

TECHNICAL FIELD

The present disclosure relates generally to the field of centralized event detection and communications. More particularly, disclosed embodiments are directed to centralized server or cloud-based communication systems for generating automated electronic messages in a facility based on detected and predicted events.

BACKGROUND

The concept of centralized command to support operations is well supported in practice and literature. Military, emergency management, aviation and other high-consequence operations have used a centralized command model to enable communication and coordination of work to achieve intended outcomes. Healthcare organizations adopted a similar model in the 1980's for use during emergencies, Hospital Emergency Incident Command System (HEICS), that has since become Hospital Incident Command System (HICS). Taking lessons from within healthcare and from other industries, the concept of a central hospital command center to support daily operations has emerged. As experience continues to grow within healthcare using the healthcare command center model, technology adoption has accelerated and is now an essential component. As technology and capabilities advance, healthcare systems are able to apply new technologies to gain better insight to how best operate these complex, distributed care systems to improve outcomes for patients, hospitals, caregivers and payors.

SUMMARY

The present disclosure is directed towards healthcare command centers. Healthcare command centers may vary in cost, scope and size. The purpose of these centers is to reduce complexity, coordinate work efforts, enhancing communication efficiency and effectiveness by providing continuous and contextual situational awareness, while enabling proactive planning for actual and potential needs. The output of these centralized and coordinated activities enables value through a concentration of operational expertise and effort reduction across a variable workforce whose primary mission is providing patient care. When patients are cared for in a system that is coordinated across the care continuum access to care is timely, length of hospitalization is reduced, direct and indirect costs of care are reduced, and potential for preventable harm is reduced. A centralized operation allows insight into resource utilization, giving visibility to peak-demand and under-use of extremely valuable infrastructure, resources, human capital and beds. A centralized command center is able to assign scarce resources to emergent patient needs, while choreographing a scheduled care plan for expected patient care activities.

Caregivers are the experts at providing clinical care to patients, supporting families, and planning for courses of treatments. In existing healthcare systems, clinicians are often overtasked with burdens of providing care, operational logistics of finding and deploying supplies and equipment, while also asked to facilitate the placement of patients into the next appropriate care setting, complete with providing an excellent patient experience free from defect or harm. The overtasking of clinicians leads to cognitive overload, which is known to be a significant factor in reduced function and contributing factor to safety events. According to the present disclosure, with the establishment of a centralized command center, the operational aspects of providing care may be offloaded to a central group of staff who develop the expertise in healthcare operations to support caregivers. Operational experts may monitor and forecast needs and deploy resources in a coordinated method to meet the needs with efficiency. Caregivers remain expert clinicians and operational experts coordinate the flow of patients and resources to support the care environment.

Existing healthcare environments are overwhelming caregivers and staff with continuous streams of information, and identifying priority messages is a growing challenge. According to the present disclosure, through the use of predictive analytics, message prioritization may be automated, and identified messages may be presented to caregivers and staff in simple, elegant notifications. The notifications may enable caregivers and staff to quickly identify the highest value work first, for completion within the constellation of activities performed each shift. Completion of high-value work first has a network effect that frees up beds, accelerates timeliness of treatments, and reduces the queuing effect of non-prioritized batched activities. Streamlining message prioritization and transmission may also reduce communication network loads by reducing redundant and unnecessary communications.

BRIEF DESCRIPTION OF THE DRAWINGS

The accompanying drawing, which is incorporated in and constitutes a part of this specification, illustrates embodiments that together with the description, serve to explain the disclosed principles.

FIG. 1 depicts an exemplary command center system, consistent with embodiments of the present disclosure.

DETAILED DESCRIPTION

Exemplary embodiments are described with reference to the accompanying drawings. In the figures, which are not necessarily drawn to scale, the left-most digit(s) of a reference number identifies the FIGURE in which the reference number first appears. Wherever convenient, the same reference numbers are used throughout the drawings to refer to the same or like parts. While examples and features of disclosed principles are described herein, modifications, adaptations, and other implementations are possible without departing from the spirit and scope of the disclosed embodiments. Also, the words "comprising," "having," "containing," and "including," and other similar forms are intended to be equivalent in meaning and be open ended in that an item or items following any one of these words is not meant to be an exhaustive listing of such item or items, or meant to be limited to only the listed item or items. It should also be noted that as used herein and in the appended claims, the singular forms "a" "an," and "the" include plural references unless the context clearly dictates otherwise.

FIG. 1 shows a diagram of a command center system 100 that may be configured to perform one or more software processes that, when executed by one or more processors, perform methods consistent with disclosed embodiments. The components and arrangements shown in FIG. 1 are not intended to limit the disclosed embodiments, as the components used to implement the disclosed processes and features may vary.

In accordance with disclosed embodiments, command center system 100 may include a facility server 130, a facility terminal 140, one or more user devices 120, and one or more network servers 160. User device 120, facility server 130, facility terminal 140, and third party server 160 may communicate directly, through network 150, through local network 110, or through a combination of communications methods.

Facility terminal 140 may be located within a centralized healthcare command center. Additionally or alternatively, facility 140 may be a standalone device placed in user 170's office, an employee station, or an alternative central location in a workplace. In some embodiments, terminal 140 may be a desktop or notebook computer, a flat panel or projected display, or any other display.

User 170 may be an employee in a workplace environment such as a physician, nurse, technician, or dispatcher. User 170 may also be an operational expert staffing the centralized command center. User 170 may operate facility terminal 140 and/or mobile device 120 or another computer (not shown) to interact with command center system 100.

User device 120 may be a personal computing device such as, for example, a general purpose or notebook computer, a mobile device with computing ability, a tablet, smartphone, wearable device such as Google Glass™ or smart watches, or any combination of these computers and/or affiliated components. In one embodiment, user device 120 may be a computer system or mobile computer device that is operated by user 170.

User device 120 may be connected to facility server 130 and/or network server 160 directly (not shown) or via a combination of one or more of local network 110 and/or network 150. Other components known to one of ordinary skill in the art may be included in system 100 to gather, process, transmit, receive, and provide account information consistent with the disclosed embodiments.

Facility server 130 may be operated by a facility such as a hospital, business, retail location, and the like. Facility server 130 may be a computer-based system including computer system components, desktop computers, workstations, tablets, hand held computing devices, memory devices, and/or internal network(s) connecting the components.

Network 150 may comprise any type of computer networking arrangement used to exchange data. For example, network 150 may be the Internet, a private data network, virtual private network using a public network, and/or other suitable connection(s) that enables system 100 to send and receive information between the components of system 100. Network 150 may also include a public switched telephone network ("PSTN") and/or a wireless network.

Local network 110 may comprise any type of computer networking arrangement used to exchange data in a localized area, such as WiFi, Bluetooth™, Ethernet, and other suitable short-range connections that enable facility terminal 140 and user device 120 to send and receive information between the components of system 100. In some embodiments, local network 110 may be excluded, and facility terminal 140 and user device 120 may communicate with system 100 components via network 150. In some embodiments, facility terminal 140 and/or user device 120 may communicate with one or more system 100 components via a direct wired or wireless connection.

Network server 160 may be a server operated by a third party entity such as a provider of networking, cloud, or backup services.

According to some embodiments, a healthcare command center may be implemented in a healthcare venue such as a hospital. A healthcare command center may also be implemented in a healthcare system encompassing a number of healthcare venues; the healthcare command center may serve as the command center for some or all of the healthcare venues within the healthcare system. A healthcare command center may provide a number of services to the healthcare venue or system. Some of the services may be executed by one or more processors. In some embodiments, services may be selected according to the needs and capacity of a healthcare venue or system. In other examples, a healthcare command center may provide all available services and tools to a healthcare venue or system. Services and tools may span a continuum of care from community health to preventative health to acute care to post-acute care to reintegration of patients back into the community.

Processors within the healthcare command center may collect and analyze data to provide situational awareness indicators. For example, one or more processors may collect data pertaining to indicators of flow of patients through a healthcare venue, system, or systems. Data may be collected from one or more sensors, aggregated from electronic medical records received from networked databases, received from input on one or more computers within system 100 or in communication with system 100. Data collection and analysis may provide predictive and cognitive analytics about future trends and events within a healthcare venue, system, or systems. A healthcare command center may use collected data to plan future events or to offer recommendations to staff or caregivers about future best practices. A healthcare command center may additionally collect contextual data in real-time. For example, a healthcare command center may collect data about current demands and availabilities across a healthcare system during a period of time. This data may be used to plan or suggest future actions using predictive and statistical analyses.

In some embodiments, a healthcare command center may collect and analyze data pertaining to a developing health condition within a community. For example, a healthcare command center may collect and analyze data pertaining to a public health emergency, a population-based illness, endemic, or epidemic, an injury pattern, or any other type of clustered health condition within a community. Examples population-based illness may include, and are not limited to, flu, MERS-CoV, Ebola, and SARS. According to one example, a healthcare command center may collect and analyze data pertaining to a developing flu epidemic within a community. The healthcare command center processor(s) may analyze the data to recognize a variety of indicators in the community and predict the developing epidemic and before sick patients arrive at healthcare facilities. For example, the healthcare command center may monitor the number of purchases of flu medicine by collecting data concerning scanned consumer product codes for flu medicine. The healthcare command center may collect this and other data from the community to determine when the flu epidemic will cause patients to seek medical attention, such as at a hospital or a clinic. The collected data may be used to assess a healthcare system's current state of affairs, such as occupancy levels, projected volumes over coming days, planned procedures, outpatient and inpatient visits, etc. This data may be used to make or suggest changes such as operational changes, supply chain changes, patient intake and discharge changes, and staffing changes, to better prepare for the predicted influx of patients with the flu. These changes may be based upon, for example, historical trends.

The following are descriptions of command center embodiments according to the present disclosure. The embodiments are not exclusive, and features of the embodiments may be included within other embodiments.

Centralized Patient Placement

In some embodiments, a command center may include develop of patient-flow management expertise in the healthcare command center workforce based on critical thinking, problem solving, teamwork and high-reliability. Such expertise may be achieved with executive sponsorship and engagement. For example, one or more of a vice president, director, manager, data analyst, and administrative support personnel may be engaged. These personnel may be engaged for a predetermined length of time; for example, between six months and one year. Patient-flow management expertise may additionally be developed by engaging front line staff, such as critical care registered nurses or a hybrid model. Patient-flow management expertise may additionally be developed by issuing and following advisories pertaining to interviewing and hiring, as well as advisories pertaining to defining of job descriptions.

Some embodiments may additionally include development of closed loop communications to end users and/or clinicians to cognitively off-load tasks related to patient movements. Some embodiments may additionally include the development and delivery of "just-in-time notifications". Through the use of analytics and applied best practices, priority messages may be identified and presented to caregivers and staff in simple, elegant notifications. The notifications may enable caregivers and staff to quickly identify the highest value work first, for completion within the constellation of activities performed each shift, thus minimizing fatigue associated with or caused by a large and overwhelming number of alarms, information, and tasks. Some embodiments may additionally include burning platform advisories.

Some embodiments may include use of, or be performed with, various computer-executed tools. For example, some embodiments may utilize patient capacity management tools, such as patient admission tracking programs, patient bed tracking programs, patient transportation tracking programs, and patient tracking portals. Some embodiments may additionally include use of tools for tracking and reporting the performance of command center staff and/or health center staff. Some embodiments may additionally include real-time locating systems (RTLS), such as auto-discharge tools.

A variety of services may also be implemented during the development and delivery of a healthcare command center. These services may include, for example, workflow redesign and automation advisories; reevaluation and advisories concerning workflow policies and procedures; integration of the healthcare command center into the healthcare center and the overarching health system; call recording systems with immediate playback and integration; phone systems with multiline conference call capability; and analytics, scorecard, and interpretation advisories, wherein baseline is established prior to go-live of automation. Services may additionally include discharge process advisories; executive and operational governance advisories; development and integration of clinical protocols, standard operating procedures, and scripts; educational practices for onboarding of staff, with annual reviews for all key stakeholders with competencies; transportation networks, both medical & non-medical; ergonomics design and selection advisories; workspace design/selection advisories; executive capacity management council advisories; and organization chart advisories.

Patient Transfer Center

Some embodiments may include design, implementation, and optimization of patient access screening and triage to available options (i.e., access as a service, not destination; right patient, right venue, right price, right now). Screening and triage may be achieved by, for example, incorporation of emergent or scheduled transfer of patients for tertiary, quaternary, and/or specialty care. Some embodiments may additionally include phone consults before a patient may be transferred, allowing expert advice to be shared between clinicians. Some embodiments may include telemedicine, such as in community hospitals, post-acute settings, skilled nursing facilities, staff homes, and other remote work sites. Some embodiments may include just-in-time ambulatory clinics or clinician office visits, as well as mobile integrated health, community-based nursing staff, and paramedic visits to home and/or work.

Some embodiments may additionally include incorporation of code teams, rapid response units, and specialty-intervention teams. Examples of such teams may include trauma care teams, stroke teams, STEMI teams, and sepsis teams. Some embodiments may include communication and coordination techniques with such teams.

Some embodiments may include use of, or be performed with, various computer-executed tools. For example, some embodiments may include use of tools for access management such as patient transfer control tools, community access tools, and on-call scheduling tools. Some embodiments may additionally include predictive insight tools.

A variety of services may also be included within some embodiments of a command center. These services may include, for example, incorporation of transportation networks, both medical and non-medical; ergonomics design and selection advisories; workspace design and selection advisories; referral network advisories; internal and external marketing advisories; and menu of services advisories, for internal and external clients.

Hospital Command Center

Some embodiments may include the design and installation of a model work environment to the health care center. This environment may include ergonomics, environmental controls, lighting, sound management, communications devices, utility services redundancy, and modular configurations. The environment may be capable of growth and may be scalable.

Some embodiments may additionally provide real-time data streams on current performance, resource availability, utilization, response-times, congestion and barriers, such as patient traffic monitoring and management. Additionally, some embodiments may provide development and application of care-progression, core-measure, and/or quality indicator measure monitoring, as well as itinerary-based choreographed patient care and real-time intervention for outliers or atypical patients. The provision of such data drives clinicians to highest value work first.

Integrated services may also be included within some embodiments, such as telemedicine, remote monitoring, asset tracking, automated supply chain, and partner and vendor-performance services. Some embodiments may also provide practice-based evidence to drive research into patient outcomes across the continuum of care.

In some embodiments, the command center may include provision of clinical workflow tools, as well as real-estate sourcing and selection advisory services, post-acute network advisory and automation services, and ambulatory network advisory and automation services.

Enterprise Healthcare Command Center

Some embodiments may include development and application of a unified communications and coordination center for patient access into, through and across health system based on standardized and automated workflows. It may utilize predictive analytics to anticipate needs based on forecasted patient activities, occupancy, demands, and length-of-stay data. This may include, for example, patient or resource capacity watches and warnings to prepare and/or take action. Some embodiments may additionally utilize conditional analytics to provide decision support on next-best choices when a primary option is not available. These choices may depend on, for example, clinical, financial, and/or operational indicators. Some embodiments may additionally include hospital network advisory services.

Regional Healthcare Fusion Center

Some embodiments may provide a population-health monitoring hub, wherein data pertaining to one or more the following is collected and analyzed: consumer-based purchases, homes, mass-gatherings, symptoms, environmental factors, seasonal factors, migratory patterns, and population disease-specific factors.

Some embodiments may additionally provide simulation-capable modeling for testing care-delivery methods, for guiding strategy, and for aiding in regional business-case planning to drive outcomes. A cloud-based emergency management hub may be implemented for the health system and may be integrated with public safety communications and incident commands. Some embodiments may additionally provide emergency and disaster preparedness advisory services, population health advisory services, telehealth advisory services, and market survey advisory services.

According to the present disclosure, healthcare command center delivery is intended to solve the problem of fragmented healthcare structure, complex and ad hoc process, leading to intentional and purposeful outcomes. Achievement of these outcomes occurs through a delivery method that may enable the creation of a healthcare command center that centralizes operations, standardizes and automates workflow, and consistently aggregates and reliably disseminates valuable information to system stakeholders.

Healthcare command center delivery may include bundled projects and non-bundled projects. According to some embodiments, one bundled option may include a potential to sell a full healthcare command center with all the supporting technology and services to support a hospital or healthcare system. According to some embodiments, non-bundle projects may centralize existing tools and workflow into a formal structure. Specialty expertise may be provided by, for example, internal subject matter experts with centralized healthcare command center design and deployment experience.

Service staff may provide project management, technical discovery and design, plan project resources, and manage team to implementation.

Integration staff may assess and plan for standard and novel integration points with the goal of high-integration into a final healthcare command center.

Advisory services may assess a current level of organizational maturity, establish executive steering group, and create a high-level roadmap to achieve a next level of maturity using strengths and resources of the healthcare command center. They may additionally lead or enable change and transition methods for a client organization.

Client success staff may manage on-going relationship across an organization to enable initial and long-term adoption coordinated with Advisory Services.

Healthcare command center SMEs may collaborate across the project from initial envisioning through post-implementation. They may provide direction on model design, best practice, staff selection, training and workflows through an iterative process with all stakeholders.

In some embodiments, a healthcare command center may be implemented according to the following exemplary method. According to some examples, the healthcare command center may be optimized periodically, based on initial impact outcomes within a first year of implementation; optimization processes and outcomes progress may be delivered within two years; and three years may allow driving to high-level outcomes while moving into a sustainment and leadership continuity phase. According to some examples, as years additional years approach (such as years four and five), redesign may be considered based on a current needs assessment and as client priorities evolve, maintaining relevance and engagement in the healthcare command center central role.

Some embodiments of a healthcare command center may include a single hospital with centralized capacity management with access management for a referral network. According to some embodiments, the healthcare command center may include patient access management tools, capacity management tools, performance reporting tools, and some limited services. According to other embodiments, the healthcare command center may include patient access management tools, capacity management tools, performance reporting products RTLS with auto-discharge tools, predicting insight tools, and comprehensive services.

Other embodiments of a healthcare command center may include single hospital management with associated referral and post-acute networks. According to some embodiments, the center may include patient access management tools, capacity management tools, performance reporting tools, and comprehensive services. According to other embodiments, the healthcare command center may include patient access management tools, capacity management tools, clinical workflow tools, performance reporting tools, RTLS with auto-discharge services, predictive insight services, comprehensive services, telemedicine, and asset tracking.

Other embodiments of a healthcare command center may include multi-hospital capacity management with referral and post-acute networks. According to some embodiments, the center may include patient access management tools, capacity management tools, predictive insight services, comprehensive services, RTLS with auto-discharge services, and asset tracking. According to other embodiments, the healthcare command center may include patient access management tools, capacity management tools, clinical workflow tools, performance reporting tools, RTLS with auto-discharge services, predictive insight services, comprehensive services, telemedicine, asset tracking, augmented and/or virtual-reality command centers.

Other embodiments of a healthcare command center may include multi-hospital and ambulatory capacity management with referral and post-acute networks, plus active public health and public safety integration. According to some embodiments, the center may include patient access management tools, capacity management tools, predictive insight services, comprehensive services, RTLS with auto-discharge services, asset tracking, post-acute integration, ambulatory and/or clinic integration. According to other embodiments, the healthcare command center may include access management tools, capacity management tools, a clinical workflow suite, performance reporting tools, RTLS with auto-discharge services, predictive insight tools, comprehensive services, telemedicine, asset tracking services, virtual-reality command centers, and community based care networks.

In some embodiments, a healthcare command center may be integrated with emergency medical services (EMS) to gain visibility into community needs. This integration may include routine medical transportation services such as ambulances and wheelchair vans, as well as integration with non-medical transportation services, such as Uber, Lyft, and taxis or other similar ride-share programs. Integration with EMS may occur at both the front-end (transportation of patients to a healthcare venue for treatment) and the back-end (transportation to post-care facilities after patient discharge), and may provide data to predict future transportation demands.

In some embodiments, front-end EMS may be integrated with the healthcare command center to provide real-time data about current demands for service and about capacities of different healthcare venues across a healthcare system. Instead of EMS services transporting all patients to an acute-care setting such as an emergency department, exemplary healthcare command centers may coordinate delivery of patients to the appropriate healthcare venue via EMS. For example, patients experiencing emergency medical situations such as stroke or heart attack may be transported to an acute-care center via EMS services such as an ambulance, while other patients experiencing less severe symptoms may be transported to an alternative venue such as an urgent care clinic via ambulance or alternatively via a different mode of transportation such as Uber or taxi. As a result, patients are transported to the appropriate venue of care, and individual venues are not overwhelmed with patients better suited for other venues.

By collecting data pertaining to transportation of patients to the correct venue care, exemplary healthcare command centers may better understand needs across a region. Collected data may better indicate needs for different venues of care such as hospitals and urgent care centers. This data may be used to plan development of specific venues within the region to better suit the demand, and may additionally be used to develop and implement telemedicine services. Collected data may additionally cause individual venues to be less overwhelmed with patients better suited for other venues. Collected data may additionally be used to predict future demands across the region, allowing planning of future venues and allocation of resources across the system that may not necessarily be aligned presently.

In some embodiments, healthcare command centers may additionally be integrated with back-end care systems that manage discharge of patients. Data collected by the healthcare command center may be used to better manage discharge needs. For example, one or more processors may determine that approximately 20% of patients from an acute-care hospital require medical transportation, such as in a wheelchair van or ambulance, to another treatment facility, such as a skilled nursing facility, acute rehab facility or post-acute rehab facility, or some other setting. Other exemplary patients may be at a venue for a medical appointment which may end at a particular time, after which they may require a ride home or to work. Healthcare command centers may monitor patient numbers and planned stay durations within a healthcare venue to scale transportation services to accommodate need over time. As a result, patients are transported quickly and do not have to wait after discharge for a transportation service to arrive to pick them up. Additionally, hospitals do not become backed up with discharged patients waiting for transportation to post-acute care venues, thus reducing numbers of extended stays. Healthcare command centers may monitor transportation needs throughout the day, week, and year to better anticipate future needs and to coordinate transportation services accordingly. Healthcare command centers may additionally monitor demand for particular type of transportation services overtime, as well as for time-sensitive discharges, such as patients who need to arrive at a secondary venue at a particular time. In this way, back-end EMS services are scalable to current and projected demand.

In some embodiments, a healthcare command center may include virtual reality systems and/or augmented reality systems integrated into the healthcare command center for simulations of the healthcare command center. These simulations may be utilized to support healthcare command center space design, workflow validation, and for training purposes. For example, an exemplary healthcare command center may provide a virtual reality simulation, for example through virtual reality (VR) goggles. The simulation may depict the spatial design of a healthcare command center, such as a planned future healthcare command center. The simulation may provide a number of templates pertaining to different features that a user may select to build a simulated healthcare command center. Templates may include, for example, transfer center resources, central bed placement resources, utilization review resources, admissions teams, financial services, and EMS and helicopter dispatch services. In the simulation, the user may lay out selected resources throughout the space to visualize how the space would look and operate. The user may additionally simulate planning over time for future needs or for future expansion of current resources. The simulation may enable the user to review a variety of factors such as the required furniture and materials, work flow, the layout of the different resources in the center, and interactions between different resources. This may enable simulated development of a team within the center. Alternatively or additionally, a plurality of users may view the same simulation, and may build a simulated healthcare command center together in the simulation.

In some embodiments, a healthcare command center may provide virtual-reality simulations and/or augmented-reality simulations to enable virtual engagement between geographically distant healthcare venues or individuals. For example, in a healthcare system with a number of hospitals which are geographically distant, users from each of those hospitals may enter into a virtual-reality simulation or an augmented-reality simulation integrated with the healthcare command center. For example, the simulation may be held in the place of a daily conference telephone call to discuss management of patient flow and the barriers to it. In the simulations, the users may view data together at the same time, and may view each other and may gesture to each other. The simulation may provide active engagement between users and may allow better sharing and analysis of data in the group setting. Alternatively or additionally, simulations may be held with multiple users to discuss complex patients who may have confounding issues. For example, a healthcare venue may admit an international patient with a set of complexities such as personal security details and embassy resources. Instead of calling or emailing sensitive data concerning this patient between users, the users may instead meet in a simulation. This may provide better sharing of information between users while allowing protection of that shared information.

In some embodiments, a healthcare command center may provide virtual-reality simulations and/or augmented-reality simulations to enable virtual healthcare command center extension to users in remote health venues. Examples of remote health venues may include ambulances and rural clinics. Users in remote health venues may benefit from periodic immersive healthcare command center team engagement. By providing these users with virtual-reality simulations, these remote users may engage users in the healthcare venue without having to travel to the venue. Additionally, simulation users may include staff and/or caregivers within a healthcare venue who do not have time to travel through the venue to a meeting room. These users may include case management workers. By holding a virtual-reality simulation instead of an in-person meeting, a case management worker may interact with other users in the simulation without having to waste time traveling to the meeting.

In some embodiments, a healthcare command center may provide virtual-reality simulations and/or augmented-reality simulations for training purposes. For example, newly hired healthcare command center staff may be trained in a virtual-reality simulation.

In some embodiments, a healthcare command center may provide virtual-reality simulations and/or augmented-reality simulations when the physical healthcare command center is inaccessible or otherwise unavailable, such as during a catastrophic failure such as a hurricane. In the event that staff cannot physically access the healthcare command center, they may hold a virtual-reality simulation instead from a safe location from which they may execute some or all of their regular duties.

In some embodiments, a healthcare command center may include agnostic call recording integration. For example, a healthcare command center may be integrated with one or more call recording services. Calls into the healthcare command center may be logged by the healthcare command center using various identifiers so that the calls may be accessed later and analyzed for trend detection and analysis. When a call is logged, a voice print from the call may be saved, as are various identifiers about the source of the call. The voice print and the associated data may be linked with one or more electronic records for later access and review. For example, when a patient places a 911 call, that call may enter the healthcare command center computer aided dispatch (CAD) system. The CAD may auto-populate the phone number, address, cross-street, local police department, first responders, and any other relevant information about the call source, and save the data with the unique identifier associated with that source. Alternatively, if the CAD receives a call from a source already associated with a unique identifier, the CAD may access that unique identifier and associated information, view historical data, and update the data if desired. In some embodiments, different call sources may each have a unique identifier with associated data and with which calls may be associated and stored. For example, individual patients and homes may have unique identifiers, as may other healthcare venues, systems, and healthcare command centers. As a result, when the healthcare command center receives a call from one of these sources, the dispatcher within the healthcare command center may view the information associated with the call to determine who is calling. The information may include historical data about the frequency of calls and the frequency of admissions. According to embodiments in which a call is received at the healthcare command center from a different healthcare venue, the call may include a unique identifier for the source of the call. The identifier may include, for example, the hospital from which the call is coming, as well as the floor number, room number, and optionally the individual placing the call. As a result, the staff member in the healthcare command center who receives the call may know the source of the call, may view data from past calls, and may log the current call into the history associated with the unique identifier. As a result, if resources are distributed as a result of the call, or if patients are transferred between healthcare venues as a result of the call, the healthcare command center may ensure that the resources and/or patients are sent to the correct venue.

Alternatively or additionally, in some embodiments, a call received at the healthcare command center may be assigned a unique patient identifier which may identify the patient or patients about whom the call concerns. As a result, the patient's record may include a history of calls relating to that patient, and the voice prints of those calls. This voice print data may be shared when the patient's record is shared between caregivers and/or between healthcare venues or systems.

In some embodiments, the patient's medical records, lab result data, transfer history, call history, and transaction case number may be associated using one or more electronic record links, for ease of access. In some embodiments, the aforementioned data may be associated with the patient's medical records, so that the medical records include historical lab result data, histories of calls about the patient, the patient's transfer history, and a history of patient's admissions across venues. This data may be maintained and updated over time.

In some embodiments, a healthcare command center may automatically generate and send end of shift reports. End of shift reports pertain to critical information collected during a given shift, such as high-level data. These reports may be sent to relevant staff and caregivers. In some existing healthcare systems, data is manually entered into the report by the shift supervisor. As a result, the report often has errors because of the manual entry, leading to an erosion of staff trust. In some embodiments, healthcare command center processors according to the present disclosure may track data during the shift in one or multiple databases, and may aggregate data from these databases to auto-generate the end of shift report. By automating generation and delivery of these reports, exemplary healthcare command centers provide crucial information to staff that is prompt and accurate. Alternatively or additionally, in some embodiments, the healthcare command center may be integrated with dashboards on a computer or personal device associated with staff and caregivers. Dashboards may provide staff and caregivers with continuous contextual information in real-time that is aggregated by and delivered from the healthcare command center. Staff and caregivers may personalize their individual dashboard to receive the most pertinent data.

In some embodiments, a healthcare command center may be integrated with an automated capacity operations status board. The board may be mounted within a healthcare venue and may provide visual indications of available capacities in specialty service units. These units may include trauma units, pediatrics, STEMI, stroke units, and neurosurgical units. Data depicted on the board may be collected, analyzed, and provided by the healthcare command center. The board may indicate the number of beds available in each unit, as well as available staff and resources. The board may indicate these available capacities visually, such as by depicting one or more of colors, numbers, letters, and symbols. For example, the board may utilize a color scheme indicating the availability in each unit, wherein a green indicator means the unit may receive additional patients with no or minimal delay in care, a yellow indicator means the unit may be capable of receiving additional patients but that resources may be limited and/or there may be a delay in care, and a red indicator means the unit may not accept any additional patients and/or may be short on resources and/or staff. The red indicator may suggest to other units and to other healthcare venues not to send additional patients to that unit, and to find a next available unit.

For example, if a unit which previously had open beds exceeds its ability to take on additional patients, the status of that unit may change in the board from green to red. A staff member or caregiver within the unit may change the indicator manually. Additionally or alternatively, processors within the healthcare command center may collect and analyze data for each unit and may execute algorithms to determine if the unit has exceeded its ability to take on additional patients. Healthcare command center processors may also execute algorithms to predict future trends in the ability of a unit to receive additional patients. If the healthcare command center determines that an indicator status change is necessary, it may automatically change the indicator without manual action by a staff member or caregiver. Alternatively, it may suggest the indicator status change to a staff member or caregiver.

According to some embodiments, the healthcare command center processors may analyze data to determine current demands on specialty service units, as well as the available capacities of each unit. Using machine learning and/or other artificial intelligence methods, the processors may generate projections of demands on each of the units and may offer suggestions to a user in response to these projections. For example, the healthcare command center may determine that a particular unit will shortly see an influx in patients due to a large traffic accident. The healthcare command center may analyze the current and projected demands of the trauma unit and may offer one or more options to the board user. For example, if the healthcare command center determines that the unit is not capable of handling additional patients after patients from the traffic accident are admitted, it may offer a first suggestion to change the indicator for that unit to red, and a second suggestion to change the indicator for that unit to yellow. The healthcare command center may prioritize one suggestion over the other. For example, the healthcare command center may suggest a red indicator as the best option and a yellow indicator as the second-best option. These prioritizations may be validated by a board user. The healthcare command center may track which suggestion the user selects in a given situation and may execute machine learning algorithms to optimize the prioritization of suggestions according to received data.

Alternatively or additionally, in some embodiments, a change in indicator status on the board may trigger automated responses from the healthcare command center and the systems controlled by the healthcare command center. For example, if a user changes the indicator for a unit to red, it may trigger mustering of additional resources and staff to send to that unit. The change in indicator may also cause the healthcare command system to generate alternative transportation plans for prospective patients. For example, if a patient plans to be transferred from a first unit to a second unit, in the case that the second unit's indicator changes to red, the healthcare command center may generate a plan to transport that patient to an alternative unit, either within the same healthcare venue or at a different healthcare venue.

In some embodiments, a healthcare command center may calculate wellness indices for all patients in a healthcare venue, and may record and track changes in indices over time. The healthcare command center may generate a baseline parameter for each patient and monitor their associated indices overtime, as compared to the baseline. In some embodiments, the healthcare command center may interface with one or more third party systems for providing collected data and receiving a calculated health index or clinical stability indicator for one or more patients. The healthcare command center may be associated with various devices throughout the healthcare venue, such as patient monitors, patient headboard devices, caregiver's personal devices, and desktop computers. Caregivers may use these devices to view the wellness indices for a given patient, as well as to view historical trend data and baseline data for that patient. Index data may be displayed in real-time. The wellness index may be used to assess the wellness of the patient. The historical data may be used to assess the patient's status overtime and whether the patient's health is improving or deteriorating.

In some embodiments, a healthcare command center may provide an on-call web based system which may perform direct messaging. Such a system may allow messaging without integration into an external phone system. The system may be connected with a scheduling program.

Various operations or functions are described herein, which may be implemented or defined as software code or instructions. Such content may be directly executable ("object" or "executable" form), source code, or difference code ("delta" or "patch" code). Software implementations of the embodiments described herein may be provided via an article of manufacture with the code or instructions stored thereon, or via a method of operating a communication interface to send data via the communication interface. A machine- or computer-readable storage medium may cause a machine to perform the functions or operations described, and includes any mechanism that stores information in a form accessible by a machine (e.g., computing device, electronic system, and the like), such as recordable/non-recordable media (e.g., read only memory (ROM), random access memory (RAM), magnetic disk storage media, optical storage media, flash memory devices, and the like). A communication interface includes any mechanism that interfaces to any of a hardwired, wireless, optical, and the like, medium to communicate to another device, such as a memory bus interface, a processor bus interface, an Internet connection, a disk controller, and the like. The communication interface can be configured by providing configuration parameters and/or sending signals to prepare the communication interface to provide a data signal describing the software content. The communication interface can be accessed via one or more commands or signals sent to the communication interface.

The present disclosure, also relates to a system for performing the operations herein. This system may be specially constructed for the required purposes, or it may include a general-purpose computer selectively activated or reconfigured by a computer program stored in the computer. Such a computer program may be stored in a computer readable storage medium, such as, but not limited to, any type of disk including floppy disks, optical disks, CDROMs, and magnetic-optical disks, read-only memories (ROMs), random access memories (RAMs), EPROMs, EEPROMs, magnetic or optical cards, or any type of media suitable for storing electronic instructions, each coupled to a computer system bus.

The order of execution or performance of the operations in embodiments illustrated and described herein is not essential, unless otherwise specified. That is, the operations may be performed in any order, unless otherwise specified, and embodiments may include additional or fewer operations than those disclosed herein. For example, it is contemplated that executing or performing a particular operation before, contemporaneously with, or after another operation is within the scope of aspects of the invention.

Embodiments may be implemented with computer-executable instructions. The computer-executable instructions may be organized into one or more computer-executable components or modules. Embodiments may be implemented with any number and organization of such components or modules. For example, aspects of the disclosure are not limited to the specific computer-executable instructions or the specific components or modules illustrated in the figures and described herein. Other embodiments may include different computer-executable instructions or components having more or less functionality than illustrated and described herein.

When introducing elements of aspects of the disclosure or the embodiments thereof, the articles "a," "an," and "the" are intended to mean that there are one or more of the elements. The terms "comprising," "including," and "having" are intended to be inclusive and mean that there may be additional elements other than the listed elements.

Having described aspects of the disclosure in detail, it will be apparent that modifications and variations are possible without departing from the scope of aspects of the disclosure as defined in the appended claims. As various changes could be made in the above constructions, products, and methods without departing from the scope of aspects of the disclosure, it is intended that all matter contained in the above description and shown in the accompanying drawings shall be interpreted as illustrative and not in a limiting sense.

What is claimed is:

1. A computerized system for automated control of flow of patients in a healthcare facility, the system comprising:
   at least one processor in communication with a communications network; and
   a storage medium comprising instructions that, when executed, configure the at least one processor to:
      receive community data, the community data comprising at least one of consumer-based purchases data, mass-gatherings data, migratory patterns data, or population disease-specific factors;
      receive facility data pertaining to one or more healthcare facilities, the facility data comprising scheduling of caregivers, delivery of health supplies to the healthcare facility, and real-time data streams on current facility performance;
      employ machine learning methods to calculate a projection for future patient flow to the healthcare facility based on the community data and the facility data, the projection comprising projected demand for each unit in the healthcare facility;
      determine whether each unit is capable for handling additional patients based on the projection;
      responsive to a determination that at least one unit is capable of handling additional patients, generate one or more first suggestions, the first suggestions comprising at least one of a room assignment of a patient within the healthcare facility based on the projection or a schedule of at least one caregiver based on the projection;
      responsive to a determination that no unit is capable of handling additional patients, generate one or more second suggestions, the second suggestions comprising a unit indicator modification; and
      display, on at least one display device mounted within the healthcare facility, a graphical user interface dashboard indicating at least one of the first suggestions or the second suggestions.

2. The computerized system of claim 1, wherein to employ machine learning methods to calculate the projection, the at least one processor is configured to perform cognitive analytics for future trends within the each of the one or more healthcare facilities based on historic trends.

3. The computerized system of claim 1, wherein
   the community data further comprises an injury pattern and epidemic information, and
   the consumer-based purchases comprise scanned consumer product codes for flu medicines.

4. The computerized system of claim 1, wherein the real-time data streams on current facility performance comprises patient admission tracking, patient bed tracking, and patient transportation tracking.

5. The computerized system of claim 4, wherein the real-time data streams on current facility performance further comprises auto-discharge data.

6. The computerized system of claim 1, wherein
   to receive community data, the at least one processor is configured to connect with a population-health monitoring hub; and
   the community data comprises the consumer-based purchases data, the mass-gatherings data, the migratory patterns data, the population disease-specific factors, and a number of patients seeking medical attention; and
   the consumer-based purchases comprise scanned consumer product codes for medicines.

7. The computerized system of claim 1, wherein
   the facility data comprises records of transportation needs throughout a day, a week, and a year; and
   the projection comprises transportation demands.

8. The computerized system of claim 7, wherein the at least one processor is further configured to:
   responsive to a determination that no unit is capable of handling additional patients, placing transportation requests with non-medical transportation services, the non-medical transportation services comprising rideshare applications.

9. The computerized system of claim 1, wherein the facility data comprises capacities of different healthcare venues across a healthcare system.

10. The computerized system of claim 9, wherein the second suggestions further comprise supply chain changes, patient intake and discharge changes, and staffing changes.

11. The computerized system of claim 10, wherein the second suggestions further comprise a workflow redesign, the workflow redesign comprising alternative screen and triage flows.

12. The computerized system of claim 9, wherein the projection comprises healthcare region demands.

13. The computerized system of claim 1, wherein the at least one processor is further configured to:
responsive to a determination that no unit is capable of handling additional patients, provide a virtual-reality simulation engaging geographically distant healthcare venues with individuals.

14. The computerized system of claim 1, wherein the community data comprises call logs comprising voice prints and source identifiers, the voice prints being linked to one or more electronic records.

15. The computerized system of claim 14, wherein the at least one processor is further configured to assign a unique patient identifiers for each call in the call logs.

16. The computerized system of claim 1, wherein the first suggestions comprise shift reports.

17. The computerized system of claim 1, wherein the graphical user interface dashboard displays virtual indications of available capacities in specialty service units, the available capacities comprising number of beds available in each unit, available resources, and available staff, each of the available capacities being color-coded.

18. The computerized system of claim 1, wherein the at least one processor is further configured to:
responsive to a determination that no unit is capable of handling additional patients:
automatically request additional resources and staff to units in the healthcare facility; and
generate alternative transportation plans for prospective patients.

19. A computerized implemented method for automated control of flow of patients in a healthcare facility, the method comprising:
receiving community data, the community data comprising at least one of consumer-based purchases data, mass-gatherings data, migratory patterns data, or population disease-specific factors;
receiving facility data pertaining to one or more healthcare facilities, the facility data comprising scheduling of caregivers, delivery of health supplies to the healthcare facility, and real-time data streams on current facility performance;
employing machine learning methods to calculate a projection for future patient flow to the healthcare facility based on the community data and the facility data, the projection comprising projected demand for each unit in the healthcare facility;
determining whether each unit is capable of handling additional patients based on the projection;
responsive to determining that at least one unit is capable of handling additional patients, generating one or more first suggestions, the first suggestions comprising at least one of a room assignment of a patient within the healthcare facility based on the projection or a schedule of at least one caregiver based on the projection;
responsive to determining that no unit is capable of handling additional patients, generating one or more second suggestions, the second suggestions comprising a unit indicator modification; and
displaying, on at least one display device mounted within the healthcare facility, a graphical user interface dashboard indicating at least one of the first suggestions or the second suggestions.

20. A non-transitory computer-readable medium storing instructions that when executed by one or more processors, cause the one or more processors to perform operations for automated control of flow of patients, the operations comprising:
receiving community data, the community data comprising at least one of consumer-based purchases data, mass-gatherings data, migratory patterns data, or population disease-specific factors;
receiving facility data pertaining to one or more healthcare facilities, the facility data comprising scheduling of caregivers, delivery of health supplies to the healthcare facility, and real-time data streams on current facility performance;
employing machine learning methods to calculate a projection for future patient flow to the healthcare facility based on the community data and the facility data, the projection comprising projected demand for each unit in the healthcare facility;
determining whether each unit is capable of handling additional patients based on the projection;
responsive to determining that at least one unit is capable of handling additional patients, generating one or more first suggestions, the first suggestions comprising at least one of a room assignment of a patient within the healthcare facility based on the projection or a schedule of at least one caregiver based on the projection;
responsive to determining that no unit is capable of handling additional patients, generating one or more second suggestions, the second suggestions comprising a unit indicator modification; and
displaying, on at least one display device mounted within the healthcare facility, a graphical user interface dashboard indicating at least one of the first suggestions or the second suggestions.

\* \* \* \* \*